United States Patent [19]

Chapuis

[11] Patent Number: 5,087,612
[45] Date of Patent: Feb. 11, 1992

[54] OXYGENATED ALICYCLIC COMPOUNDS AND THEIR USE IN PERFUMERY

[75] Inventor: Christian Chapuis, Grand-Saconnex, Switzerland

[73] Assignee: Firmenich SA, Geneva, Switzerland

[21] Appl. No.: 577,408

[22] Filed: Sep. 4, 1990

[30] Foreign Application Priority Data

Sep. 25, 1989 [CH] Switzerland .................... 3472/89
Oct. 3, 1989 [CH] Switzerland .................... 3613/89

[51] Int. Cl.$^5$ .............................................. A61K 7/46
[52] U.S. Cl. ................................ 512/23; 568/666; 568/670; 568/376
[58] Field of Search .............. 512/23; 568/376, 670, 568/878

[56] References Cited

U.S. PATENT DOCUMENTS

| | | | |
|---|---|---|---|
| 1,873,430 | 8/1932 | Knorr et al. ........................... | 47/32 |
| 3,308,172 | 3/1967 | Rudner et al. ....................... | 568/878 |
| 3,859,366 | 1/1975 | Schleppnik ........................... | 568/878 |
| 4,252,986 | 2/1981 | Klein et al. .......................... | 568/822 |
| 4,313,855 | 2/1982 | Klein et al. .......................... | 252/522 R |
| 4,459,425 | 7/1984 | Amano et al. ....................... | 568/666 |
| 4,608,445 | 8/1986 | Giersch et al. ...................... | 568/670 |
| 4,626,602 | 12/1986 | Schulte-Elte ........................ | 568/822 |
| 4,698,180 | 10/1987 | Pavlin ................................... | 568/670 |

FOREIGN PATENT DOCUMENTS

| | | | |
|---|---|---|---|
| 0080148 | 6/1983 | European Pat. Off. ............ | 568/666 |
| 0081699 | 6/1983 | European Pat. Off. ............ | 568/667 |
| 0121828 | 10/1984 | European Pat. Off. ............ | 568/822 |
| 1964405 | 7/1971 | Fed. Rep. of Germany ...... | 568/880 |
| 2418214 | 9/1979 | France ................................ | 568/822 |

*Primary Examiner*—James H. Reamer
*Attorney, Agent, or Firm*—Pennie & Edmonds

[57] ABSTRACT

A compound of formula

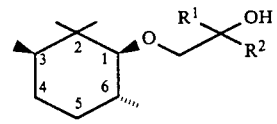

wherein $R^1$ represents a hydrogen atom or a saturated, linear or branched, alkyl radical, having from 1 to 4 carbon atoms, and $R^2$ designates a lower alkyl radical, saturated or unsaturated, linear or branched;

or any mixture containing a predominant amount of said compound (I), together with its isomer of formula

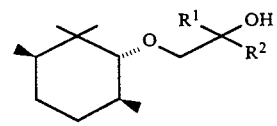

wherein $R^1$ and $R^2$ are defined as above.

Compounds (I) and their mixtures mentioned above develop odor notes of the woody-amber type and are therefore used as perfuming ingredients for the preparation of perfuming compositions and perfumed articles.

A process for the preparation of compounds (I) and their mixtures is disclosed.

21 Claims, No Drawings

OXYGENATED ALICYCLIC COMPOUNDS AND THEIR USE IN PERFUMERY

BRIEF SUMMARY OF THE INVENTION

The present invention relates to the perfume industry. It concerns more particularly, a compound of formula

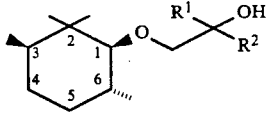
(I)

wherein $R^1$ represents a hydrogen atom or a saturated, linear or branched, alkyl radical, having from 1 to 4 carbon atoms, and $R^2$ designates a lower alkyl radical, saturated or unsaturated, linear or branched;

or any mixture containing a predominant amount of said compound (I), together with its isomer of formula

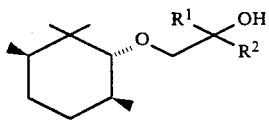
(II)

wherein $R^1$ and $R^2$ are defined as above.

The invention also concerns a method to confer, enhance, improve or modify the odor properties of a perfuming composition or a perfumed article, which method comprises adding to said composition or article a fragrance effective amount of a compound of formula (I) as defined in claim 1, or of a mixture of said compound (I) with its isomer of formula (II) as defined in claim 1.

Further objects of the invention include a perfuming composition or a perfumed article containing as active ingredient a compound of formula (I) or a mixture as defined above.

The invention provides equally a process for the preparation of a compound of formula (I) as defined in claim 1, or of a mixture of said compound (I) with its isomer of formula (II) as defined in claim 1, said process comprising the reaction, under the Grignard type reaction conditions, of a compound of formula

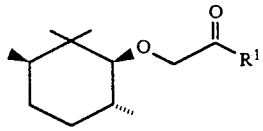
(VI)

wherein $R^1$ is defined as in formula (I), or of a mixture containing a predominant amount of said compound (VI), with an organometallic compound of formula $R^2MgX$, wherein X stands for a halogen atom and $R^2$ is defined as in formula (I).

BACKGROUND OF THE INVENTION

European Patent No. 0081898 discloses compounds of formula

$$X'-CH_2-CHOH-CH_2-R'$$

wherein R' stands for an alkyl radical containing from 1 to 3 carbon atoms and X' designates a substituted cyclohexyloxy radical having the formula

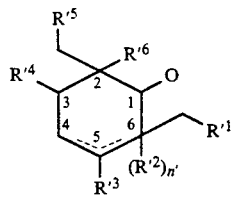

wherein index n' stands for 0 or 1, the dotted lines indicate the location of a single (n'=1) or double bond in position 2 (n'=0) or 3 (n'=1) and each of symbols $R'^1$ to $R'^6$ designates a hydrogen atom or a methyl radical. It is also disclosed in the above-cited patent that these prior art compounds possess useful odor properties, namely that they develop an "elegant woody-amber odor, warm and rising, enriched by a slightly animal tonality reminiscent of natural amber, occasionally slightly fruity or floral, as the case may be". Finally, it is further cited in the prior art reference that the above-mentioned compounds can take various isomeric forms which are capable of developing, in parallel with their basic woody-amber note, other olfactive nuances. Nevertheless, it is mentioned that, for practical and economical reasons, preferred use is made of the stereoisomers mixtures.

Careful analysis of the cited prior art actually shows that no particular interest in one or another of said stereoisomeric forms was recognized at the time and that their individual organoleptic properties went undetected or were not judged sufficiently discriminating to justify the use of one isomer in particular, rather than that of the mixture of isomers. As a matter of fact, the examples of the use of these compounds in perfumery which are described in EP 0081898 relate strictly to the use of mixtures of undiscriminated isomers, in spite of the fact that specific isomeric forms were described for at least one compound, i.e., the isomers of formula

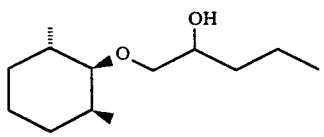

and

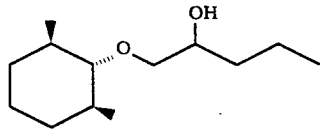

Moreover, the olfactive description of the two isomers, which are said to possess, respectively, a slightly woody and a woody-perspiration note, would not have suggested to the man in the art any particular advantage in using one of the specific stereoisomeric forms rather than the mixture, nor have made it possible for him to predict that individual isomers of these or other analogous compounds could be useful in their own right and have distinctive properties, as has presently been found.

THE INVENTION

It has now been discovered that the novel compounds, which are the object of the present invention, represented by the formula

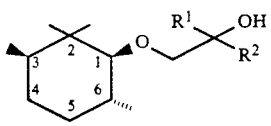 (I)

wherein $R^1$ represents a hydrogen atom or a saturated, linear or branched, alkyl radical, having from 1 to 4 carbon atoms, and $R^2$ designates a lower alkyl radical, saturated or unsaturated, linear or branched;

as well as the mixtures cited above which contain a predominant amount of compound (I), possess very useful odor properties which complement and provide the perfumer's palette with an enriching variety of nuances in the area of the fragrant compounds with woody-type odors.

By lower alkyl radical it is understood here any alkyl radical having from 1 to 4 carbon atoms.

We have in fact been able to ascertain that there is a particularly marked difference between the olfactive properties of said compounds (I) and those of their cis isomers of formula

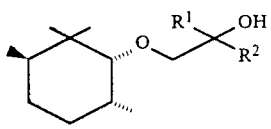 (III)

or

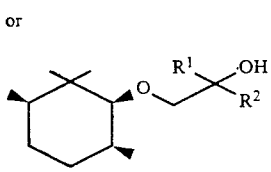 (IV)

wherein $R^1$ and $R^2$ are defined as in formula (I). Whenever trans and cis configurations are cited herein, they are meant to refer to the relative orientations of the substituting groups in positions 1 and 6 of the ring.

Compounds (I), and the mixtures defined above which contain a predominant amount of one of said compounds, are perfuming ingredients of remarkably greater value than their cis isomers (III) or (IV). Their odor notes are in fact more powerful and tenacious, and have a more useful character than those of said cis isomers, and compounds (I) are therefore also better perfuming ingredients than any mixture of isomers which contains a considerable amount of cis isomers (III) or (IV).

The preceding conclusions were arrived at as a result of comparative evaluations carried out by perfumer experts on the compounds and mixtures which are the object of the invention, in relation to prior known compounds of similar structure. For example, 1-(2,2,c-3,t-6-tetramethyl-r-1-cyclohexyloxy)-2-pentanol, a preferred compound of the invention, was found to have a distinct odor note from that of a prior art mixture which contained 51% by weight of this compound, together with 28% of its corresponding isomer of formula (III), or 1-(2,2,t-3,c-6-tetramethyl-r-1-cyclohexyloxy)-2-pentanol, and 21% of corresponding isomer of formula (IV), or 1-(2,2,c-3,c-6-tetramethyl-r-1-cyclohexyloxy)-2-pentanol. While the prior art mixture mentioned above possessed a woody-amber note, with an unclear animal character which was clouded by a perspiration note, and with a dusty and almost fruity nuance, the compound of the invention, or 1-(2,2,c-3,t-6-tetramethyl-r-1-cyclohexyloxy)-2-pentanol developed a woody-amber odor note where the animal character was clear and dominant, and entirely devoid of the perspiration note.

The fragrance of this latter compound turned out to be much clearer, cleaner and more powerful than that of the cited isomeric mixture. Furthermore, the olfactive evaluation of the isomers with a cis conformation established their responsibility for the dusty, fruity, perspiration odor note identified in said mixture and which devaluates the latter, from an olfactive point of view, relative to 1-(2,2,c-3,t-6-tetramethyl-r-1-cyclohexyloxy)-2-pentanol.

These olfactive differences between the above-cited compound of the present invention and the mixture of isomers disclosed in the prior art cited above, and namely the superiority of the former over the latter, were also observed, albeit with some variations, when the mixture was compared to other compounds (I) according to the invention, as can be ascertained from the examples presented further on.

The odor properties of the compounds of formula (I) appear as all the more surprising when one considers that there are many examples in the prior art of useful fragrant compounds possessing woody-type notes and the structures of which are similar to those of compounds (I) according to the invention. One might therefore have expected the latter to bring no original and unexpected contribution to the perfumer's palette. Yet, exactly the opposite has been observed.

In this context, European patent No. 0121828 is a particularly pertinent example. It discloses the use in perfumery of cycloaliphatic alcohols of formula

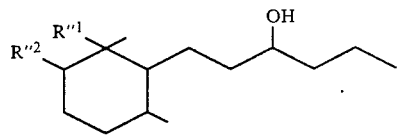 (V)

wherein each of the symbols $R''^1$ and $R''^2$ designates a methyl radical, or $R''^1$ stands for an ethyl radical and $R''^2$ for a methyl radical or hydrogen. The stereoisomers of these compounds having a trans configuration, defined by the formula

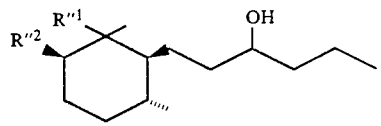

are judged to be clearly superior to their isomers, from an olfactive point of view, and are said to develop woody-amber notes with a very marked animal character. These notes are described as being remarkably powerful. Amongst the compounds described, 1-(2,2,3,6-tetramethyl-1-cyclohexyl)-3-hexanol (mixture consisting essentially of isomer c-3,t-6) is a well-appreciated perfuming ingredient, whose powerful animal note is now part of many commercial fragrances. In the context of the present disclosure, this compound is cited as a reference for comparison, which respect to the compounds (I) according to the present invention.

The following Table I summarizes the odor properties of preferred compounds of the invention and compares the strength, tenacity and olfactive quality of their note relative to that of above-mentioned 1-(2,2,3,6-tetramethyl-1-cyclohexyl)-3-hexanol.

cation, depending on the perfuming effect that one wants to achieve and the nature of the product to be perfumed.

Moreover, it is also apparent from Table I that, although the tenacity and strength of the fragrances of compounds (I) are inferior to those of prior known compound A), the performance of the compounds according to the present invention, and particularly that of 1-(2,2,c-3,t-6-tetramethyl-r-1-cyclohexyloxy)-2-pen-

TABLE I

Odor properties of compounds of formula (I) and comparative evaluation with those of prior art 1-(2,2,c-3,t-6-tetramethyl-r-1-cyclohexyl)-3-hexanol

| Reference | Compound | Olfactive evaluation |
|---|---|---|
| A) | [structure] | very powerful woody, amber, animal note |
| 1) | [structure] | nicely woody-amber, warm, elegant and deep note; more velvety than that of A), less tenacious and less powerful but still excellent; of an easier use than A) for the same type of applications |
| 2) | [structure] | similar note to that of 1), just as rich and woody but lightened by a fruity, floral, creamy and vaguely spicy tonality; less tenacious than 1), comparable strength |
| 3) | [structure] | quite woody character, more tenacious note than that of 2), comparable to that of 1), but with an irone-type and floral nuance, reminiscent of the salicylates |
| 4) | [structure] | woody-amber note, with a "pencil", dust tonality, less powerful than the preceding, spicy bottom note, weakly tenacious |
| 5) | [structure] | weaker and less ambery note than that of 1), with a limestone, papier mache, dust nuance; good tenacity comparable to that of 3) |
| 6) | [structure] | woody note, with a dust, old board of yard timber nuance, without the amber character; good tenacity comparable to 3) |
| 7) | [structure] | woody-amber note, of medium strength, with mouldy, earthy nuances |
| 8) | [structure] | woody, camphoraceous note, almost borneolic, medium tenacity, weaker than the preceding |

This table shows that, in spite of the structural similarity between compounds (I), each of these compounds has distinct odor qualities from those of the others. Thus, each compound can be used for a particular application, 1-(2,2,c-3,t-6-tetramethyl-r-1-cyclohexyloxy)-4-penten-2-ol or 1-(2,2,c-3,t-6-tetramethyl-r-1-cyclohexyloxy)-2-butanol, cited as preferred compounds of the invention, turns out to be just as good when the quality of their odor notes is taken into consideration. Compounds (I) are even found to be of an "easier" application than the prior art compound of reference, as a result of the fact that their animal note is less dominant and aggressive than that of said known compound. Therefore, compounds (I) may very well be used as alternative perfuming ingredients to 1-(2,2,3,6-tetramethyl-1-cyclohexyl)-3-hexanol, depending on the type of application envisaged and have the advantage of forming a varied olfactive ensemble that enriches the perfumer's choice, each compound being susceptible of privileged use in a particular application. These conclusions are quite apparent from the results of the perfumery application and comparison examples presented further on.

As cited before, the novel mixtures of isomers which contain a predominant amount of compound (I), together with the corresponding isomer of trans configuration represented by formula (II), are also the object of the present invention. By a predominant amount it is to be understood here any proportion of compound (I) which is not inferior to 60% by weight, with respect to the total weight of the mixture. Mixtures of these two isomers which contain 75% or more, by weight, of compound (I) and 25% or less of compound (II) are preferred according to the invention.

Although the cis isomers of formula (III) or (IV) were consistently judged to be olfactively inferior to their trans counterparts of formula (I) or (II), mixtures of isomers which do not contain more than a total amount of 10% by weight of compounds (III) and/or (IV) were found to be perfectly adapted to the perfumery use according to the present invention and could be advantageous for less costly applications.

It goes without saying that the present mixtures of isomers are clearly advantageous when compared to those described in the prior art of reference which contained much higher amounts of cis isomers.

The compounds of formula (I) and their mixtures according to the invention can be used with equal advantage in fine and in technical perfumery. They are particularly adapted to the preparation of perfuming compositions of varied nature, namely of the floral type, to which they impart a ground note of rich and elegant woody character, without overdominance from the accompanying animal tonality. They find an equally advantageous use in the preparation of various perfumed articles such as soaps, shower or bath gels, shampoos, cosmetic preparations, body or air deodorants, detergents, fabric softeners or yet perfumes, Colognes and shaving lotions.

The proportions in which compounds (I) may be used for the above-mentioned applications vary in a wide range of values. The man in the art knows by experience that such proportions are a function of a perfuming effect which is desired to achieve, as well as of the nature of the product to be perfumed. As an example, concentrations of the order of 1 to 10%, or even 20% by weight, with respect to the weight of the composition to which they are added, can be used. Much lower concentrations may however be used when compounds (I) are applied in soaps, toiletries, cosmetics or detergents and fabric softeners.

As a result of their olfactive qualities, the compounds of the invention may be widely used in perfumery, either on their own, by direct addition to the products one desires to perfume, or, as is more common, previously diluted in solvents of current use such as ethanol, anozol or diethyl phthalate and in admixture with other perfuming ingredients of synthetic or natural origin.

The present invention also provides a process for the preparation of a compound of formula (I) as defined in claim 1, or of a mixture of said compound (I) with its isomer of formula (II) as defined in claim 1, said process comprising the reaction, under the Grignard type reaction conditions, of a compound of formula

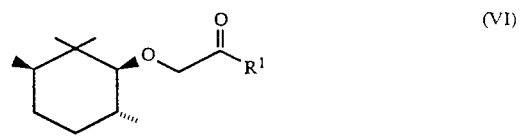

wherein $R^1$ is defined as in formula (I), or of a mixture containing a predominant amount of said compound (VI), with an organometallic compound of formula $R^2MgX$, wherein X stands for a halogen atom and $R^2$ is defined as in formula (I).

Novel compounds (VI), used as starting products in the process of the invention, can be prepared from 2,2,3,6-tetramethyl-1-cyclohexanone (isomer mixture consisting essentially of the trans isomer) according to the process represented schematically below:

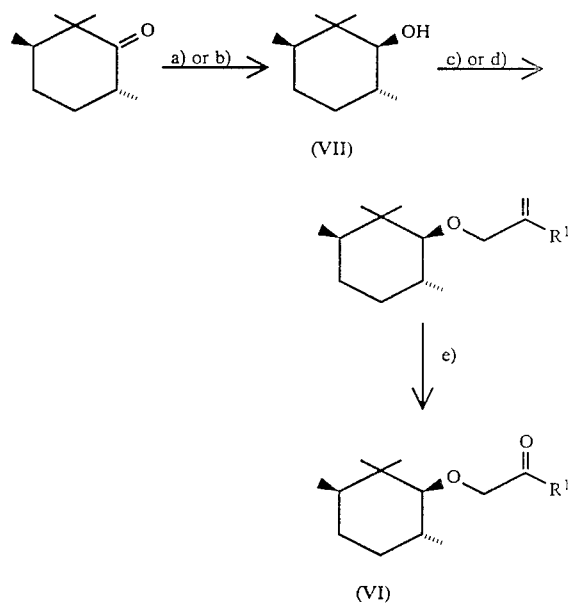

a) Na, isopropanol, toluene
b) Li, NH$_3$, isopropanol c) butyllithium, THF, $R^1\overset{O}{\underset{\|}{C}}\diagup\diagdown X$ d) Li, styrene, THF, toluene, $R^1\overset{O}{\underset{\|}{C}}\diagup\diagdown X$ e) O$_3$, MeOH, Na$_2$SO$_3$, H$_2$O
X = Cl or Br
$R^1$ defined as above 2,2,3,6-Tetramethyl-1-cyclohexanone, essentially in its trans configuration illustrated above, can be prepared according to the method described by G. Schäppi and C. F. Seidel [see Helv. Chim. Acta 30, 2199 (1947)].

The first step in the process illustrated above is a reduction of the ketone represented. The product of this reaction is a mixture containing essentially 2,2,c-3,t-6-tetramethyl-r-1-cyclohexanol (VII), as well as minor quantities of the three stereoisomers of formula

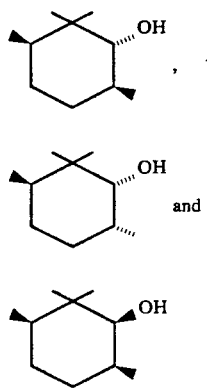

(VIII), (IX) and (X)

The reaction conditions were optimized to obtain a mixture as enriched in alcohol (VII) as possible and having a very weak global content in isomers cis of formulae (IX) and (X), so as to guaranty the stereochemical purity of the compound of formula (VI) used as starting product in the process according to the invention. Thus, it was discovered that this aim was best achieved whenever a solution of the starting ketone in isopropanol was added to a refluxing solution of lithium in ammonia [see under b) above], following a method analogous to that described by J. W. Huffman et al. in J. Am. Chem. Soc. 90, 6486 (1968).

The specific conditions of this reaction are described in the preparation examples presented further on. This process provided a mixture containing around 79% of alcohol (VII), 17% of alcohol (VIII) and respectively 1 and 3% of cis stereoisomers, alcohols (IX) and (X). The desired alcohol (VII) was isolated by means of two successive recrystallizations of this mixture from pentane. However, owing to the weak global content of said mixture in isomers (IX) and (X) (around 4%), it could also be used as such in the following step of the process illustrated above.

The reduction of 2,2,3,6-tetramethyl-1-cyclohexanol under the conditions described under letter a) of the scheme above provided a mixture with the following composition: 73% (VII)+18% (VIII)+5% (IX)+4% (X).

When classical conditions for reducing alicyclic ketones were used, mixtures of alcohols much richer in cis isomers were obtained. For example, the use of LiAlH$_4$, in the presence of ethyl ether, starting from the same product, yielded a mixture of alcohols containing 51% of (VII), 28% of (IX) and 21% of (X). Likewise, the use of NaBH$_4$ in ethanol, or of hydrogen in the presence of platinum oxide and acetic acid, led to mixtures which contained isomers (IX) and (X) in quantities comparable to the mixture's content in alcohol (VII).

The allylation of alcohol (VII), or of the mixture enriched in alcohols (VII) and (VIII), had a better yield when the reaction was carried out by means of a strong base such as n-butyllithium, or still better, lithium, in the presence of tetrahydrofuran and, in the second case, styrene.

The ozonolysis of the allyloxy derivative obtained in the preceding reaction, followed by a reducing extraction of the formed ozonide by means of aqueous Na$_2$SO$_3$, provided the desired compound (VI). When the starting product in the allylation reaction was one of the cited mixtures enriched in alcohols (VII) and (VIII), the ozonolysis product was a mixture enriched in compound (VI), together with lower quantities of its isomer derived from trans alcohol (VIII). Since the allylation and ozonolysis reactions take place with retention of the starting product's stereochemistry, these final mixtures enriched in one of compounds (VI) contained at least 70% in weight of the latter and less than 10% in weight of the corresponding cis isomers, with respect to the total weight of the mixture.

According to the invention, the compounds of formula (I) are prepared via the reaction of a compound of formula (VI), obtained as described above, with a Grignard reagent of formula $R^2MgX$ previously defined.

Alternatively, as starting product in the process of the invention, a mixture of isomers enriched in compound of formula (VI), as defined above, was used to yield a mixture enriched in stereoisomers of formulae (I) and (II). The latter could be further enriched in compound (I) if desired, or provide pure compound of formula (VI), by means of the usual techniques such as gas chromatography. Preferably, the mixture used as starting product contained at least about 75% by weight of the compound of formula (VI) and not more than about 10% by weight of the two cis isomers derived from alcohols (IX) and (X), the rest of the mixture being formed by the other trans isomer derived from alcohol (VIII).

The process according to the invention is described in a more detailed manner in the following preparation examples, wherein the temperatures are indicated in degrees centigrade and the abbreviations have the usual meaning in the art. Examples of the application of compounds of formula (I) and their mixtures according to the invention in perfuming compositions and perfumed articles are also described hereinafter.

EXAMPLES 1 TO 22

Grignard Reaction: General Method

A flask fitted with a mechanical stirrer was charged with 0.12 mol of magnesium and 25 ml of THF (tetrahydrofuran) or of ether. The reaction was triggered with a small iodine crystal and a few drops of methyl iodide. A solution of 0.12 mol of the appropriate halide in 25 ml of either THF or ether was then added dropwise (the temperature rose to reflux). After 30 min stirring until all the magnesium had been consumed, 0.1 mol of the chosen aldehyde, respectively ketone, were added dropwise (the temperature rose to reflux). The reaction mixture was stirred for 1 h, respectively 2 h, at room temperature and then poured on ice and NH$_4$Cl, extracted with ether, washed with NH$_4$Cl, neutralized, dried and concentrated.

According to this method, the following compounds were prepared.

1) 1-(2,2,c-3,t-6-tetramethyl-r-1-cyclohexyloxy)-2-pentanol from 79.7 g (0.402 mol) of the aldehyde prepared as described further on and 66 ml (0.72 mol) of propyl bromide, in THF. After distillation on residue and then on a spinning band column, the desired product 96% pure was obtained, in the form of a mixture containing around 80% of the above-cited isomer and 20% of 1-(2,2,t-3,t-6-tetramethyl-r-1-cyclohexyloxy)-2-pentanol.

Yield: 59%; B.p. 55°/4.8 Pa

Analytical data of 1-(2,2,c-3,t-6-tetramethyl-r-1-cyclohexyloxy)-2-pentanol:

IR: 3450 (—OH), 1100(—O—) cm$^{-1}$
NMR(360 MHz, $^1$H): 0.74–0.98(m,15H)); 2.42(d,J=10.8Hz,1H); 3.33–3.62(m,2H); 3.79(m,1H) δ ppm
MS: M$^+$=242(43); m/e: 157(30), 138(96), 123(38), 109(15), 96(20), 87(19), 83(39), 69(37), 55(59), 41(100)

Olfactive evaluation: see Table I.

2) 1-(2,2,c-3,t-6-tetramethyl-r-1-cyclohexyloxy)-4-penten-2-ol from 5.0 g (25 mmol) of the aldehyde prepared as described further on, in 8.2 g of THF, and allyl bromide. Bulb-to-bulb distillation on residue yielded 3.6 g of the desired product 44% pure. The latter was chromatographed on SiO$_2$, using a 5:1 mixture of petroleum ether/sulphuric ether as elution agent, to provide 0.6 g of a 98% pure product, in the form of a mixture containing 85% of the above-cited isomer and 15% of 1-(2,2,t-3,t-6-tetramethyl-r-1-cyclohexyloxy)-4-penten-2-ol.

Yield: 18%

Analytical data of 1-(2,2,c-3,t-6-tetramethyl-r-1-cyclohexyloxy)-4-penten-2-ol:

IR: 3450 (—OH) cm$^{-1}$
NMR(360 MHz,$^1$H): 0.74(d,J=7 Hz,3H); 0.82(d,J=7 Hz,3H); 0.96(s,6H); 2.43(d,J=11 Hz,1H); 3.40–3.62(m,2H); 5.8(d,J=9 Hz,1H); 5.25(d,J=17 Hz,1H); 5.85(m,1H) δ ppm
MS: M$^+$=240(6); m/e: 155(16), 38(60), 123(28), 96(40), 83(100), 69(70)

Olfactive evaluation: see Table I.

3) 1-(2,2,c-3,t-6-tetramethyl-r-1-cyclohexyloxy)-2-butanol from 8.0 g (40 mmol) of the aldehyde prepared as described further on and ethyl bromide, in 10.9 g of THF. After distillation on a Vigreux column, 5.35 g of a 80% pure product were obtained. Further purification of the latter provided the pure product as a mixture containing 85% of the desired isomer mentioned above and 15% of 1-(2,2,t-3,t-6-tetramethyl-r-1-cyclohexyloxy)-2-butanol.

Yield: 46%; B.p. 61°/4.2 Pa

Analytical data of 1-(2,2,c-3,t-6-tetramethyl-r-1-cyclohexyloxy)-2-butanol:

IR: 3450 (—OH), 1090(—O—) cm$^{-1}$
NMR(360 MHz,$^1$H): 0.74(d,3H); 0.83(d,3H); 0.96(s,6H); 0.97(t,3H); 2.43(d,J≈10.8 Hz,1H); 3.36–3.63(m,2H); 3.70(m,1H) δ ppm
MS: M$^+$=228(43); m/e: 156(3), 143(31), 138(100), 123(39), 109(21), 96(32), 83(62), 73(51), 55(85), 41(67)

Olfactive evaluation: see Table I.

4) 2-methyl-1-(2,2,c-3,t-6-tetramethyl-r-1-cyclohexyloxy)-2-butanol from 8.0 g (38 mmol) of the ketone prepared as described further on and ethyl bromide, in 8.8 g of THF. After distillation on a spinning band column, 4.75 g of a 88% pure product were obtained. This product was further purified to provide a 99% pure mixture containing 93% of the desired isomer and 7% of 2-methyl-1-(2,2,t-3,t-6-tetramethyl-r-1-cyclohexyloxy)-2-butanol.

Yield: 46%; B.p. 45°/5 Pa

IR: 3450, 2950, 1460, 1100 cm$^{-1}$
NMR(360 MHz,$^1$H): (major isomer): 0.82(d,J=7 Hz,3H); 0.96(s,3H); 1.17(s,3H); 2.43(d,J=11 Hz,1H); 3.43(AB,J$_1$=9 Hz, J$_2$=32 Hz,2H) δ ppm. (minor isomer): 2.78(d,J=11 Hz,1H); 3.38(AB, J$_1$=8 Hz,J$_2$=36 Hz,2H) δ ppm.
MS: (major isomer): M$^+$=242(1); m/e: 170(20), 139(28), 83(100), 73(81), 69(53), 55(45). (minor isomer): M$^+$=242(2); m/e: 170(20), 139(28), 123(23), 83(100), 73(80), 69(61), 55(53).

Olfactive evaluation: see Table I.

5) 4-methyl-1-(2,2,c-3,t-6-tetramethyl-r-1-cyclohexyloxy)-2-pentanol from the aldehyde prepared as described further on (73.0 g, 0.37 mol) and isobutyl bromide, in THF (88.2 g), following the Grignard method described above.

This compound was also prepared by hydrogenation of 4-methyl-1-(2,2,c-3,t-6-tetramethyl-r-1-cyclohexyloxy)-4-penten-2-ol [the preparation of the latter is described under 11)] as follows: 1.9 g (7.5 mmol) of said pentenol, in admixture with 20 ml of ethanol and 500 mg of Raney-Ni, were hydrogenated over 18 h, at room temperature, in a 1-neck flask equipped with hydrogen inlet (effective hydrogen consumption: 250 ml). After filtering the reaction mixture on CELITE ® and concentrating, 2.0 g of raw product were obtained which were finely distilled on a bulb-to-bulb apparatus. 1.5 g of a 95% pure product were thus isolated in the form of a mixture containing 82% of the desired isomer and 18% of 4-methyl-1-(2,2,c-3,c-6-tetramethyl-r-1-cyclohexyloxy)-2-pentanol.

Yield: 73%; B.p. 80°–85°/5 Pa

Analytical data of 4-methyl-1-(2,2,c-3,t-6-tetramethyl-r-1-cyclohexyloxy)-2-pentanol:

IR: 3450(—OH), 1090(—O—) cm$^{-1}$
NMR(360 MHz,$^1$H): 0.74(d,3H); 0.82(d,3H); 0.93(s,3H); 0.95(s,3H); 0.98(d,6H); 2.42(d,J≈10.8 Hz,1H); 3.33–3.60(m,2H); 3.87(m,1H) δ ppm
MS: M$^+$=256(56); m/e: 171(21), 156(5), 138(100), 123(40), 101(17), 96(35), 83(81), 69(52), 55(79), 43(87)

Olfactive evaluation: see Table I.

6) 2-methyl-1-(2,2,c-3,t-6-tetramethyl-r-1-cyclohexyloxy)-2-propanol from 40.0 g (0.19 mol) of the ketone prepared as described further on, in 43.7 g of ether, with methyl iodide. After distillation on residue, 35.6 g of 83% pure product were obtained. Further purification of the latter provided a 98% pure product in the form of a mixture containing 79% of the desired isomer, 14% of 2-methyl-1-(2,2,t-3,t-6-tetramethyl-r-1-cyclohexyloxy)-2-propanol and 7% of 2-methyl-1-(2,2,t-3,c-6-tetramethyl-r-1-cyclohexyloxy)-2-propanol.

Yield: 68%; B.p. 72°/5 Pa

IR: 3400, 2900, 1450, 1090 cm$^{-1}$ c-3,t-6 isomer (79%)
NMR(360 MHz,$^1$H): 0.76(d,3H); 0.83(d,J=7 Hz,3H); 0.95(d,J=7 Hz,3H); 0.96(s,3H); 1.21(s,3H); 1.24(s,3H); 2.43(d,J=11 Hz,1H); 3.4(AB, J$_1$=7 Hz,J$_2$=23 Hz,2H) δ ppm
MS: M$^+$=228(14); m/e: 170(52), 139(52), 123(35), 96(35), 83(98), 69(59), 59(80), 55(100), 43(92)

t-3,t-6 isomer (14%)
NMR(360 MHz,$^1$H): 2.79(d,J=11 Hz,1H); 3.36(AB,J$_1$=7 Hz,J$_2$=16 Hz,2H) δ ppm
MS: M$^+$=228(30); m/e: 170(31), 139(59), 123(39), 83(100), 69(66), 55(86), 51(68)

t-3,c-6 isomer (7%)
MS: M$^+$=228(15); m/e: 170(35), 139(46), 123(34), 83(100), 69(68), 59(70), 55(91), 41(74)

Olfactive evaluation: see Table I.

7) 2-methyl-1-(2,2,c-3,t-6-tetramethyl-r-1-cyclohexyloxy)-4-penten-2-ol from allyl bromide and 8.0 g (38 mol) of the ketone prepared as described further on, in THF (9.8 g). Distillation on a spinning band column provided a 93% pure product which was further improved to 99% purity. The latter consisted of a mixture containing 98% of the desired isomer and 2% of 2-methyl-1-(2,2,t-3,t-6-tetramethyl-r-1-cyclohexyloxy)-4-penten-2-ol.

Yield: 60%; B.p. 57°/5 Pa
IR: 3450, 2950, 1640, 1460, 1100 cm$^{-1}$
major isomer (98%)
NMR(360 MHz,$^1$H): 0.75(s,3H); 0.82(d,J=7 Hz,3H); 0.95(d,J=7 Hz,3H); 0.97(s,3H); 1.2(s,3H); 2.3(m,2H); 2.43(d,J=11 Hz,1H); 3.4(AB,J$_1$=7 Hz, J$_2$=46 Hz,2H); 5.09(d,J=15 Hz,2H); 5.87(m,1H) δ ppm
MS: M$^+$=254(1); m/e: 170(14), 139(41), 83(100), 69(50), 57(38), 43(48)
minor isomer (2%)
NMR(360 MHz,$^1$H): 2.78(d,J=11 Hz,1H) δ ppm
MS: M$^+$=254(0); m/e: 170(17), 139(47), 83(100), 69(53), 55(43), 43(55)
Olfactive evaluation: see Table I.

8) 1-(2,2,c-3,t-6-tetramethyl-r-1-cyclohexyloxy)-3-penten-2-ol from 1-bromopropene and 10.0 g (50 mmol) of the aldehyde prepared as described further on, in THF (10.8 g). After bulb-to-bulb distillation on residue, then finely on a spinning band column, 6.6 g of a 97% pure product were obtained and further purified to yield the desired product 99% pure.

Yield: 53%; B.p. 64°/2.5 Pa
Analytical data of 1-(2,2,c-3,t-6-tetramethyl-r-1-cyclohexyloxy)-3-penten-2-ol:
NMR(360 MHz,$^1$H): 0.75 and 0.76(2s,1.5 and 1.5H); 0.83(d,J=7 Hz,3H); 0.97(d,J=7 Hz,3H); 0.98 and 0.99(2s,1.5 and 1.5H); 1.69 and 1.71(2t, J=3 Hz,1.5 and 1.5H); 2.43(d,J=11 Hz,1H); 3.48(m,2H); 4.66(m,1H); 5.38(m,1H); 5.63(m,1H) δ ppm
MS: M$^+$=240(0); m/e: 139(30), 83(100), 69(58), 55(34), 43(16)
Olfactive evaluation: see Table I.

9) 1-(2,2,c-3,t-6-tetramethyl-r-1-cyclohexyloxy)-2-hexanol from n-butyl bromide and 3.1 g (15.6 mmol) of the aldehyde prepared as described further on, in absolute THF (3.2 g, 33% pure). After purification on a SiO$_2$ column using as elution agent a 95:5 mixture of cyclohexane/acetic ether, 300 mg of a 91% pure mixture were isolated. This mixture contained 85% of the isomer cited above and 15% of 1-(2,2,t-3,t-6-tetramethyl-r-1-cyclohexyloxy)-2-hexanol.

A separate synthesis of the desired hexanol provided a 99% pure mixture of the desired c-3,t-6 isomer (95%) with the t-3,t-6 isomer (5%) cited.

Yield: ≈26%
Analytical data of 1-(2,2,c-3,t-6-tetramethyl-r-1-cyclohexyloxy)-2-hexanol:
IR: 3450 (—OH), 1090(—O—) cm$^{-1}$
NMR(360 MHz,$^1$H): 0.74(d,3H); 0.82(d,3H); 0.91(t,3H); 0.96(s,6H); 2.43(d, J≈10.8 Hz,1H); 3.36-3.62(m,2H); 3.78(m,1H) δ ppm
MS: M$^+$=256(47); m/e: 171(19), 156(4), 138(100), 123(38), 109(18), 96(33), 83(71), 69(40), 55(62), 41(81)
Olfactive evaluation: woody, camphor.

10) 3-methyl-1-(2,2,c-3,t-6-tetramethyl-r-1-cyclohexyloxy)-2-butanol from isobutyl iodide and 6.2 g (31 mmol) of the aldehyde whose preparation is described further on, in 6.5 g of absolute ether. Distillation provided 3.35 g of a 52% pure product containing 83% of the desired alcohol, 14% of 3-methyl-1-(2,2,t-3,t-6-tetramethyl-r-1-cyclohexyloxy)-2-butanol and 3% of 3-methyl-1-(2,2,t-3,c-6-tetramethyl-r-1-cyclohexyloxy)-2-butanol.

Further purification of this product by chromatography on a SiO$_2$ column, using a 95:5 mixture of cyclohexane/acetic ether as elution agent, yielded a 98% pure mixture containing 85% of 3-methyl-1-(2,2,c-3,t-6-tetramethyl-r-1-cyclohexyloxy)-2-butanol and 15% of 3-methyl-1-(2,2,t-3,t-6-tetramethyl-r-1-cyclohexyloxy)-2-butanol.

Yield: 23%
Analytical data of 3-methyl-1-(2,2,c-3,t-6-tetramethyl-r-1-cyclohexyloxy)-2-butanol:
IR: 3450 (—OH), 1090(—O—) cm$^{-1}$
NMR(360 MHz,$^1$H): 0.73(d,3H); 0.82(d,3H); 0.90(d,6H); 0.96(s,3H); 0.98(s,3H); 2.42(d,J≈10.8 Hz,1H); 3.42-3.56(m,2H); 3.63(m,1H) δ ppm
MS: M$^+$=242(48); m/e: 199(2), 181(1), 170(3), 157(22), 138(100), 123(40), 109(21), 96(30), 87(39), 83(63), 69(58), 55(69), 43(81)
Olfactive evaluation: woody.

11) 4-methyl-1-(2,2,c-3,t-6-tetramethyl-r-1-cyclohexyloxy)-4-penten-2-ol from 2-methylallyl chloride and 17.0 g (86 mmol) of the aldehyde prepared as described further on, in absolute THF (24.2 g). After distillation on a Vigreux column, 3.6 g of a 71% pure product were obtained. This product was further purified by chromatography on a SiO$_2$ column using cyclohexane/acetic ether (95:5) as elution agent. The final product, 95% pure, consisted of a mixture containing 85% of 4-methyl-1-(2,2,c-3,t-6-tetramethyl-r-1-cyclohexyloxy)-4-penten-2-ol and 15% of 4-methyl-1-(2,2,t-3,t-6-tetramethyl-r-1-cyclohexyloxy)-4-penten-2-ol.

Yield: 11%; B.p. 88°/4.6 Pa
Analytical data of 4-methyl-1-(2,2,c-3,t-6-tetramethyl-r-1-cyclohexyloxy)-4-penten-2-ol:
IR: 3450(—OH), 1090(—O—) cm$^{-1}$
NMR(360 MHz,$^1$H): 0.75(d,3H); 0.82(d,3H); 0.96(s,3H); 0.98(s,3H); 1.78(s,3H); 2.20(m,2H); 2.43(d,J≈10.8 Hz,1H); 3.41-3.62(m,2H); 3.97(m,1H); 4.82(d,J≈16.2 Hz,2H) δ ppm
MS: M$^+$=254(7); m/e: 198(7), 169(1), 156(2), 139(51), 123(21), 114(7), 109(12), 101(30), 96(21), 83(61), 69(31), 55(50), 43(100)
Olfactive evaluation: woody, slightly amber.

12) 1-(2,2,c-3,t-6-tetramethyl-r-1-cyclohexyloxy)-3-buten-2-ol from vinyl bromide and 9.75 g (49 mmol) of the aldehyde prepared as described further on, in 14.8 g of THF. Bulb-to-bulb distillation on residue, followed by distillation on a spinning band column, provided a 96% pure product (1.3 g). Further purification of the latter yielded a 99% pure mixture of the above-cited isomer (85%) with 1-(2,2,t-3,t-6-tetramethyl-r-1-cyclohexyloxy)-3-buten-2-ol (15%).

Yield: 11%; B.p. 55°/6.7 Pa
Analytical data of 1-(2,2,c-3,t-6-tetramethyl-r-1-cyclohexyloxy)-3-buten-2-ol:
IR: 3450(—OH), 2900(—CH$_2$—), 1100(—O—) cm$^{-1}$
NMR(360 MHz,$^1$H): 0.83(d,J=7 Hz,3H); 0.97(d,J=7 Hz,3H); 0.97(s,6H); 2.44(d,J=11 Hz,1H); 3.40-3.66(m,2H); 4.31(m,1H); 5.19(d,J=10 Hz,1H); 5.36(d,J=16 Hz,1H); 5.85(m,1H) δ ppm
MS: M$^+$=226; m/e: 154(5), 139(55), 123(35), 109(8), 95(36), 91(7), 83(100), 69(40), 55(42), 41(29)
Olfactive evaluation: woody, spicy, amber.

13) 1-(2,2,c-3,t-6-tetramethyl-r-1-cyclohexyloxy)-2-propanol from methyl iodide and 17.4 g (88 mmol) of the aldehyde prepared as described further on, in 19.7 g of ether/absolute THF. After fine distillation on a spinning band column, 7.1 g of a 92% pure product were obtained. This product was further purified to give a 95% pure mixture containing 86% of the desired propanol, 9% of 1-(2,2,t-3,t-6-tetramethyl-r-1-cyclohexyloxy)-2-propanol and 5% of 1-(2,2,c-3,c-6-tetramethyl-r-1-cyclohexyloxy)-2-propanol.

Yield: 34%; B.p. 45°/2.3 Pa

Analytical data of 1-(2,2,c-3,t-6-tetramethyl-r-1-cyclohexyloxy)-2-propanol:

IR: 3350(—OH), 1080(—O—) cm$^{-1}$

NMR(360 MHz,$^1$H): 0.74(d,3H); 0.82(d,3H); 0.96(s,6H); 1.14(dxd,3H); 2.43(d,J≈10.8 Hz,1H); 3.29-3.58(m,2H); 3.92(m,1H) δ ppm MS: M$^+$=214(21); m/e: 171(1), 156(1), 138(100), 129(47), 123(51), 113(4), 109(31), 96(61), 83(98), 71(92), 59(93), 55(82), 41(72)

Olfactive evaluation: woody, celluloid, camphor.

14) 2-methyl-1-(2,2,c-3,t-6-tetramethyl-r-1-cyclohexyloxy)-2-pentanol from propyl bromide and 6.4 g (30 mmol) of the ketone prepared as described further on, in 7.9 g of THF. Fine distillation on a spinning band column provided 2.9 g of the desired alcohol, 90% pure. A further purification of this product gave the same alcohol with a purity of 97%.

Yield: 33%; B.p. 47°/2 Pa

Analytical data of 2-methyl-1-(2,2,c-3,t-6-tetramethyl-r-1-cyclohexyloxy)-2-pentanol:

IR: 3450, 2950, 1460, 1100 cm$^{-1}$

NMR(360 MHz,$^1$H): 0.75(s,3H); 0.83(d,J=7 Hz,3H); 0.95(d,J=7 Hz,3H); 0.96(s,3H); 1.19(s,3H); 2.42(d,J=11 Hz,1H); 3.4(AB,J$_1$=8 Hz, J$_2$=40 Hz,2H) δ ppm MS: M$^+$=256(0.5); m/e: 170(34), 139(36), 87(77), 83(100), 69(43), 55(45), 43(29)

Olfactive evaluation: amber, woody, camphor.

15) 2,4-dimethyl-1-(2,2,c-3,t-6-tetramethyl-r-1-cyclohexyloxy)-2-pentanol a. This compound was prepared according to the above-described Grignard method, starting from methyl iodide and 3.5 g (14 mmol) of 4-methyl-1-(2,2,c-3,t-6-tetramethyl-1-cyclohexyloxy)-2-pentanone (prepared as described below under b.), in ether (3.85 g). The product obtained was bulb-to-bulb distilled on residue and then chromatographed on a SiO$_2$ column, using a 95:5 mixture of cyclohexane/acetic ether as elution agent. 3.15 g of a 96% pure mixture, containing 96% of the desired pentanol and 4% of 2,4-dimethyl-1-(2,2,t-3,t-6-tetramethyl-r-1-cyclohexyloxy)-2-pentanol, were thus obtained.

Yield: 78%

IR: 3600, 2940, 1460, 1100 cm$^{-1}$ major isomer (96%)

NMR(360 MHz,$^1$H): 0.75 and 0.76(2s, 1.5 and 1.5H); 0.82(d,J=7 Hz, 3H); 0.95(d,J=7 Hz,3H); 0.97(s,3H); 1.2 and 1.23(2s,1.5 and 1.5H); 2.42(d,J=11 Hz,1H); 3.39(AB and δ,J$_1$=7 Hz,J$_2$=36 Hz,1 and 1H) δ ppm MS: M$^+$=270(0); m/e: 170(19), 139(22), 101(68), 83(100), 69(50), 55(57), 43(40)

minor isomer (4%)

NMR(360 MHz,$^1$H): 2.78(d,J=11 Hz,1H) δ ppm

MS: M$^+$=270(0); m/e: 170(18), 139(22), 101(59), 83(100)

Olfactive evaluation: woody, cheesy nuance.

b. 4-methyl-1-(2,2,c-3,t-6-tetramethyl-r-1-cyclohexyloxy)-2-pentanone A 4-neck flask fitted with a mechanical stirrer was charged with 200 ml of concentrated acetic acid and 25 ml of H$_2$O. 21.6 g (216 mmol) of chromium trioxide were added and the mixture was cooled to 0° (ice and salt). Then, 13.8 g (54 mmol) of 4-methyl-1-(2,2,c-3,t-6-tetramethyl-r-1-cyclohexyloxy)-2-pentanol [see under 5)] were added dropwise while the temperature was kept below 0°, and the mixture was stirred for a further 30 min. After adding 30% NaOH at a temperature not higher than 20°, the reaction mixture was extracted with ether, washed to neutrality with H$_2$O, dried and concentrated: 12.05 g of raw product were thus obtained. This raw product was finely distilled on a spinning band column to give 4.5 g of a 93% pure product consisting of a mixture of the desired ketone (97%) together with 4-methyl-1-(2,2-t-3,t-6-tetramethyl-r-1-cyclohexyloxy)-2-pentanone.

Yield: 30%; B.p. 53°/3 Pa

IR: 2960, 1720, 1460, 1365, 1110 cm$^{-1}$ major isomer (97%)

NMR(360 MHz,$^1$H): 0.8(s,3H); 0.83(d,J=7 Hz,3H); 0.94(d,J=7 Hz,3H); 0.95(s,3H); 2.42(d,J=11 Hz,1H); 4.13(AB,J$_1$=15 Hz,J$_2$=22 Hz,2H) δ ppm MS: M$^+$=254(0); m/e: 155(9), 139(26), 83(100), 69(32), 57(36), 41(21)

minor isomer (3%)

NMR(360 MHz,$^1$H): 2.77(d,J=11 Hz,1H) δ ppm

MS: M$^+$=254(0); m/e: 139(20), 83(100), 69(39), 57(38), 41(22)

16) 2-methyl-1-(2,2,c-3,t-6-tetramethyl-r-1-cyclohexyloxy)-3-buten-2-ol from vinyl bromide and 6.55 g (31 mmol) of the ketone prepared as described further on, in THF (7.7 g). After fine distillation on a spinning band column, 4.55 g of a 91% pure product were obtained and further purified to give a 95% pure mixture containing 80% of the above-mentioned butenol and 20% of 2-methyl-1-(2,2,t-3,t-6-tetramethyl-r-1-cyclohexyloxy)-3-buten-2ol. major isomer (80%)

NMR(360 MHz,$^1$H): 0.72 and 0.75(s,1.2 and 1.8H); 0.82 and 0.83(d,J=7 Hz,1.2 and 1.8H); 0.94(d,J=7 Hz,3H); 0.95 and 0.97(s,1.2 and 1.8H); 1.26 and 1.30(s,1.2 and 1.8H); 2.42 and 2.43(d,J=11 Hz,0.4 and 0.6H); 3.45(AB,J$_1$=7 Hz,J$_2$=30 Hz,2H); 5.1(d,J=10 Hz,1H); 5.31(d,J=16 Hz,1H); 5.94(m,1H) δ ppm MS: M$^+$=240(0); m/e: 139(28), 123(20), 83(100), 69(44), 55(47), 43(36)

minor isomer (20%)

NMR(360 MHz,$^1$H): 2.78(d,J=11 Hz,1H); 3.41(AB,J$_1$=12 Hz,J$_2$=16 Hz,2H) δ ppm MS: M$^+$=240(0); m/e: 139(28), 123(22), 83(100), 69(44), 55(53), 43(40)

Olfactive evaluation: woody, weak.

17) 2,3-dimethyl-1-(2,2,c-3,t-6-tetramethyl-r-1-cyclohexyloxy)-2-butanol from 2-bromopropane and 6.5 g (31 mmole) of the ketone prepared as described further on, in THF (7.2 g). Fine distillation on a spinning band column afforded 2.05 g of a 75% pure product. Further purification of the latter by chromatography on a SiO$_2$ column, using as elution agent a 95:5 mixture of cyclohexane/acetic ether gave the desired alcohol 99% pure.

Yield: 20%; B.p. 47°/2 Pa

IR: 3570, 2950, 1460, 1100 cm$^{-1}$

NMR(360 MHz,$^1$H): 0.74 and 0.76(2s,1.5 and 1.5H); 0.82(d,J=7 Hz,3H); 0.88(2d,J=7 Hz,6H); 0.96(d,J=7 Hz,3H); 0.97(s,3H); 1.07 and 1.11(2s,1.5 and 1.5H); 1.85(hept,J=7 Hz,1H); 2.43(d,J=11 Hz,1H); 3.46(2AB,J$_1$=7 Hz,J$_2$=58 Hz,J$_{11}$=7 Hz,J$_{12}$=22 Hz,1 and 1H) δ ppm MS: M$^+$=256(0); m/e: 170(21), 139(29), 123(21), 87(79), 83(100), 69(46), 55(36), 42(33)

18) 3-methyl-1-(2,2,c-3,t-6-tetramethyl-1-cyclohexyloxy)-3-buten-2-ol from 2-bromopropene and 10.0 g (50 mmol) of the aldehyde prepared as described further on, in THF (12.0 g). The reaction product was bulb-to-bulb distilled on residue (9.2 g of product) and then finely distilled on a spinning band column. 6.85 g of the desired butenol 88% pure were thus obtained. Further purification by chromatography provided a 98% pure product.

Yield: 49%; B.p. 42°/3 Pa

IR: 3460, 2960, 1650, 1450, 1100 cm$^{-1}$

NMR(360 MHz,$^1$H): 0.74 and 0.75(2s,1.5 and 1.5H); 0.83(d,J=7 Hz,3H); 0.97(d,J=7 Hz,3H); 0.97(s,3H); 1.75(s,3H); 2.14(d,J=11 Hz,1H); 3.55(m,2H); 4.26(dxd,J$_1$=7 Hz,J$_2$=4 Hz,1H); 4.91(s,1H); 5.05(s,1H) δ ppm MS: M$^+$=240(0); m/e: 139(18), 83(100), 69(50), 55(28), 41(14)

Olfactive evaluation: woody.

19) 3-methyl-1-(2',2'-c-3',t-6'-tetramethyl-r-1'-cyclohexyloxy)-4-penten-2-ol from crotyl chloride and 10.0 g (50 mmol) of the aldehyde prepared as described further on, in THF (11.2 g). After bulb-to-bulb distillation on residue, then fine distillation on a spinning band column, 6.9 g of a mixture containing 96% of the desired alcohol, 2% of 3-methyl-1-(2',2',t-3',t-6'-tetramethyl-r-1'-cyclohexyloxy)-4-penten-2-ol and 2% of 3-methyl-1-(2',2',c-3',c-6'-tetramethyl-r-1'-cyclohexyloxy)-4-penten-2-ol were obtained.

Yield: 49%; B.p. 64°/2 Pa

IR: 3500, 3100, 2920, 1640, 1100 cm$^{-1}$ isomer c-3',t-6'(2 diastereomers —OH, threo/erythro 52%/44%)

NMR(360 MHz,$^1$H): 0.73 and 0.74(2s,1.3 and 1.7H); 0.82(d,J=7 Hz,3H); 0.96(s,3H); 0.97(d,J=7 Hz,3H); 1.05 and 1.09(2d,J=7 Hz,1.7 and 1.3H); 2.32(m,1H); 2.42(d,J=11 Hz,1H); 3.56(m,3H); 5.05(m,2H); 5.74(m,0.41H); 5.85(m,0.52H) δ ppm MS (52%): M$^+$=254(23); m/e: 169(17), 139(93), 123(41), 83(100), 69(72), 55(89)

MS (44%): M$^+$=254(19); m/e: 169(17), 139(90), 123(39), 83(100), 69(72), 55(86)

isomer t-3',t-6'

NMR(360 MHz,$^1$H): 2.77(d,J=11 Hz,1H) δ ppm

MS: M$^+$=254(20); m/e: 169(14), 138(77), 123(30), 96(30), 83(95), 69(59), 55(83), 43(100)

Olfactive evaluation: woody.

20) 1-(2,2,c-3,t-6-tetramethyl-r-1-cyclohexyloxy)-5-hexen-2-ol from 4-bromo-1-butene and 5.0 g (25 mmol) of the aldehyde prepared as described further on, in THF (6.1 g). Distillation on a spinning band column provided 3.4 g of a 94% pure mixture, containing 98% of the desired alcohol and 2% of 1-(2,2,t-3,t-6-tetramethyl-r-1-cyclohexyloxy)-5-hexen-2-ol. This mixture was further purified to 99% purity.

Yield: 50%; B.p. 53°/2.1 Pa

IR: 3450, 3100, 2920, 1640, 1450, 1100 cm$^{-1}$ major isomer (98%)

NMR(360 MHz,$^1$H): 0.73 and 0.74(2s,1.5 and 1.5H); 0.82(d,J=7 Hz,3H); 0.94(d,J=7 Hz,3H); 0.95 and 0.98(2s,1.5 and 1.5H); 2.2(m,2H); 2.42(d,J=11 Hz,1H); 3.5(m,2H); 3.8(m,1H); 4.97(d,J=11 Hz,1H); 5.04(d,J=15 Hz,1H); 5.83(m,1H) δ ppm MS: M$^+$=254(1); m/e: 138(54), 123(30), 96(48), 83(100), 69(65), 55(78), 43(70)

minor isomer (2%)

NMR(360 MHz,$^1$H): 2.78(d,J=11 Hz,1H) δ ppm

MS: M$^+$=254(0); m/e: 138(50), 123(33), 96(33), 83(100), 69(61), 55(90), 43(68)

Olfactive evaluation: woody.

21) 2-ethyl-1-(2,2,c-3,t-6-tetramethyl-r-1-cyclohexyloxy)-2-butanol.

a. This compound was prepared from 1-(2,2,c-3,t-6-tetramethyl-r-1-cyclohexyloxy)-2-butanone [see preparation of under b.; 7.0 g, 31 mmol)] and bromoethane, in THF (8.4 g). Fine distillation on a spinning band column afforded 2.3 g of a 95% pure product consisting of a mixture containing 60% of the desired butanol and 40% of a non-interesting side product, 2,2,c-3,t-6-tetramethyl-r-1-cyclohexyl-2-hydroxy-2-methyl-butanoate.

Yield: 28%; B.p. 40°/2.5 Pa

Analytical data of 2-ethyl-1-(2,2,c-3,t-6-tetramethyl-r-1-cyclohexyloxy)-2-butanol:

IR: 3500, 2950, 1460, 1100 cm$^{-1}$

NMR(360 MHz,$^1$H): 0.74(s,3H); 0.82(d,J=7 Hz,3H); 0.87 and 0.88(2t,J=7 Hz,3 and 3H); 0.96(d,J=7 Hz,3H); 0.97(s,3H); 2.42(d,J=11 Hz, 1H); 3.43(AB,J$_1$=7 Hz,J$_2$=15 Hz,2H) δ ppm MS: M$^+$=256(0); m/e: 170(26), 139(29), 87(85), 83(100), 69(43), 55(43), 43(28)

b. 1-(2,2,c-3,t-6-tetramethyl-r-1-cyclohexyloxy)-2-butanone.

A 4-neck flask equipped with mechanical stirring was charged with 900 ml of concentrated acetic acid and 100 ml of water. 97 g (0.97 mol) of chromium trioxide were added and the mixture was cooled to 0° (ice/salt mixture). 55.25 g (0.24 mol) of 1-(2,2,c-3,t-6-tetramethyl-r-1-cyclohexyloxy)-2-butanol [see under 3)] were added dropwise keeping the temperature at or below 0°. The mixture was stirred overnight at room temperature. Then, 30% NaOH was added while maintaining the temperature at or below 20°, and the reaction mixture was extracted with ether, washed to neutrality with water, dried and concentrated. 44.0 g of raw product were thus obtained which were purified by distillation on residue on a Vigreux column to give 26.45 g of a 76% pure mixture, containing 70% of the above-mentioned butanone and 30% of a side product, 2,2,c-3,t-6-tetramethyl-r-1-cyclohexyl-2-oxobutanoate.

Yield: 37%; B.p. 64°/6.6 Pa

Analytical data of 1-(2,2,c-3,t-6-tetramethyl-r-1-cyclohexyloxy)-2-butanone:

NMR(360 MHz,$^1$H): 0.8(s,3H); 0.83(d,J=7 Hz,3H); 0.93(d,J=7 Hz,3H); 0.95(s,3H); 1.07(t,J=7 Hz,3H); 2.42(d,J=11 Hz,1H); 2.62(q,J=7 Hz,2H); 4.14(AB,J$_1$=15 Hz,J$_2$=26 Hz,2H) δ ppm MS: M$^+$=226(1); m/e: 155(9), 139(28), 83(100), 69(33), 57(30), 43(14)

22) 3-(2,2,c-3,t-6-tetramethyl-r-1-cyclohexyloxymethyl)-1-penten-3-ol from vinyl bromide and 7.0 g (31 mmol) of 1-(2,2,c-3,t-6-tetramethyl-r-1-cyclohexyloxy)-2-butanone, according to the general Grignard method, in THF (8.4 g). After fine distillation on a spinning band column. 2.3 g of a 96% pure mixture were obtained, the mixture containing 60% of the desired pentenol and 40% of a side-product, i.e. 2,2,c-3,t-6-tetramethyl-r-1-cyclohexyl-2-ethyl-2-hydroxy-3-butenoate.

Yield: 28%; B.p. 40°/2.3 Pa

Analytical data of 3-(2,2,c-3,t-6-tetramethyl-r-1-cyclohexyloxy-methyl)-1-penten-3-ol:

IR: 3500, 2950, 1725, 1460, 1380, 1240, 1100 cm$^{-1}$

NMR(360 MHz, $^1$H): 0.71 and 0.74(2s,1.2 and 1.8H); 0.81 and 0,.82(2d, J=7 Hz, 1.2 and 1.8H); 0.89(t,J=7 Hz,3H); 0.95 and 0.97(2s,1.2 and 1.8H); 0.96(d,J=7 Hz,3H); 2.41 and 2.42(d,J=11 Hz,0.4 and 0.6H); 3.48(AB,J$_1$=7 Hz, J$_2$=15 Hz,2H); 5.17(d,J=11 Hz,1H); 5.31(d,J=15 Hz, 1H); 5.81(m,1H) δ ppm MS: $M^+=254(0)$; m/e: 139(30), 116(26), 83(100), 69(48), 57(51), 43(34)

The aldehyde and ketone used as starting products in the preceding examples were prepared as follows.

I. Preparation of (2,2,c-3,t-6-tetramethyl-r-1-cyclohexyloxy)acetaldehyde a) 2,2,c-3,t-6-tetramethyl-r-1-cyclohexanol A) A flask fitted with a mechanical stirrer was charged with 1500 ml of toluene and 92.0 g (4 mol) of sodium cut in small pieces. The reaction mixture was heated to reflux and a mixture of 154.0 g (1 mol) of 2,2,3,6-tetramethyl-1-cyclohexanone (80% trans) with 610 ml (8 mol) of isopropanol was added dropwise. After stirring for 1½ h at reflux, the mixture was left under stirring, at room temperature, overnight. Around 200 ml of ethanol were added to destroy the remaining sodium. The mixture was poured on ice, extracted with ether, washed twice with water, concentrated on a Vigreux column at atmospheric pressure and then distilled under vacuum (water pump). 151.65 g of a 96% pure mixture of alcohols was obtained, containing 73% of the desired isomer and 27% of other isomers.

Yield: 93%; B.p. 64°/6.8×10² Pa

B) A mechanically stirred flask was charged with 7.63 g (1.09 mol) of lithium and into it 1200 ml of ammonia were condensed via a $CO_2$/acetone condenser. A mixture of 60.0 g (0.39 mol) of 2,2,3,6-tetramethylcyclohexanone (80% trans), 45 ml (0.59 mol) of isopropanol and 80 ml of ether was added dropwise while refluxing the ammonia. The latter was allowed to evaporate over the week-end and some isopropanol was added to destroy the lithium excess. The reaction mixture was poured on ice, extracted with ether, washed to neutrality with saturated $NH_4Cl$, dried and concentrated by distilling on a 25 cm Vigreux column. A 96% pure crystalline mixture of alcohols (60.5 g) was thus obtained, which contained around 79% of 2,2,c-3,t-6-tetramethyl-r-1-cyclohexanol, 17% of 2,2,t-3,t-6-tetramethyl-r-1-cyclohexanol, 3% of 2,2,c-3,c-6-tetramethyl-r-1-cyclohexanol and 1% of 2,2,t-3,c-6-tetramethyl-r-1-cyclohexanol (yield: 95%; b.p. 73°/6.2×10² Pa).

Recrystallization of this mixture from pentane, twice, afforded the pure desired isomer with 58% yield.

The analytical data of 2,2,c-3,t-6-tetramethyl-r-1-cyclohexanol were as follows:

M.p.: 57°–58°

IR: 3300 (—OH) cm$^{-1}$

NMR(360 MHz,$^1$H): 0.73(s,3H); 0.85(d,J=6.5 Hz,3H); 0.97(d,J=6.5 Hz,3H); 0.99(s,3H); 2.76(d,J≈10.4 Hz,1H) δ ppm MS: $M^+=156(30)$; m/e: 138(9), 123(41), 109(15), 99(5), 95(28), 91(1), 87(2), 83(31), 77(3), 70(52), 67(13), 65(2); 57(51), 55(76), 53(13), 51(2), 45(15), 43(93), 41(100), 39(47)

b) r-1-allyloxy-2,2,c-3,t-6-tetramethylcyclohexane.

C) A flask equipped with a mechanical stirrer was charged with 60.0 g (0.38 mol) of the mixture obtained in a) B) and 600 ml of THF. 282 ml (0.42 mol) of 1.5M butyllithium in hexane were added dropwise (the temperature increased to 45°). After stirring for 1 h at room temperature, the mixture was heated to reflux, 36 ml (0.42 mol) of allyl bromide were added dropwise and the mixture was stirred overnight at reflux. A further 22 ml of allyl bromide (+60%) were then added dropwise at reflux. The reaction evolution was followed by G. C. After 6 h, 20 ml of bromide were added (+55%) and the whole was stirred at reflux over the weekend. After cooling to room temperature, the reaction mixture was poured on ice, extracted with ether, washed to neutrality with water, dried and concentrated. 88.9 g of raw product were thus obtained and they were distilled on a 20 cm column filled with glass helices. A 93% pure product was isolated (50.45 g) consisting of a 88:12 mixture of, respectively, r-1-allyloxy-2,2,c-3,t-6-tetramethylcyclohexane and r-1-allyloxy-2,2,t-3,t-6-tetramethyl-cyclohexane.

Yield: 62%; B.p.: 73°/6.2×10² Pa

IR: 1090 (—O—) cm$^{-1}$

NMR(360 MHz,$^1$H): 0.76(s,3H); 0.82(d,J=6 Hz,3H); 0.96(d,J=6 Hz,3H); 0.97(s,3H); 2.43[d,J≈10.8 Hz,10.8 Hz,0.88H,(c-3,t-6)]; 2.78[d,J≈10.8 Hz,0.12H,(t-3,t-6)]; 4.08(m,2H); 5.13(d,J=9 Hz,1H); 5.28(large d,J=16 Hz,1H); 5.96(m,1H) δ ppm MS: $M^+=196(10)$; m/e: 138(14), 123(14), 111(17), 96(16), 83(20), 69(45), 50(52), 41(100)

D) A mechanically stirred 4-neck flask was charged with 360 ml of THF, 720 ml of toluene (1:2 solution), 315.75 g (2.02 mol) of the alcohol mixture obtained in a) B) and 15.6 g (2.2 mol) of granulated lithium. The mixture was heated to 35° and a solution of 231.6 g of styrene in 360 ml of THF was added dropwise, slowly, by means of a "CFG Prominent" pump, at 140 ml/h. After refluxing for 1½ h until all the lithium had disappeared, 240 ml (2.8 mol) of allyl bromide in 230 ml of DMSO (dimethylsulfoxide) were added slowly at reflux, at 100 ml/h. The reaction mixture was heated to reflux for another hour, then cooled, poured on ice, extracted with ether, washed to neutrality with water, dried and concentrated. The raw product obtained (533.1 g) was distilled on a 20 cm column filled with glass helices and equipped with a total reflux head. 369.95 g of 92% pure product were thus obtained (yield: 85%; b.p. 77°/4.4×10² Pa). The analytical data of this product were identical to those presented in the preceding section.

c) A double walled flask fitted with mechanical stirring was charged with 79.65 g (0.406 mol) of the product obtained in b) (93% pure) and 700 ml of methanol, and cooled to −10°. An ozone current was made to bubble across the solution for 3 h. After purging with nitrogen, the reaction mixture was poured bit by bit on a solution of 56.3 g (0.45 mol) of sodium sulfite in 415 ml of water at 0°. The methanol was concentrated, the mixture was decanted, washed once with water, dried and concentrated to give 87.4 g of raw product which was used as such as the starting aldehyde in the Grignard reactions previously described. A few grams of pure product were isolated, in the form of a 80:20 mixture of, respectively, (2,2,c-3,t-6-tetramethyl-r-1-cyclohexyloxy)acetaldehyde and (2,2,t-3,t-6-tetramethyl-r-1-cyclohexyloxy)acetaldehyde.

IR: 1720 (—CHO), 1100 (—O—) cm$^{-1}$

NMR(360 MHz,$^1$H): 0.74–0.98(m,12H); 2.47(d,J=≈10.8 Hz,0.8H); 2.81(d,J≈10.8 Hz,0.2H); 4.18(AB,$J_1$=18 Hz,Δυ=29 Hz,2H); 9.78(s,1H) δ ppm MS: $M^+=198(9)$; m/e: 169(2), 154(3), 139(62), 123(18), 113(18), 109(9), 97(17), 83(75), 69(51), 55(98), 41(100)

II. Preparation of 1-(2,2,c-3,t-6-tetramethyl-r-1-cyclohexyloxy)-2-propanone a) r-1,2,2,t-4-tetramethyl-c-3-(2-methyl-2-propenyloxy)cyclohexane A 4-neck flask equipped with a mechanical stirrer was charged with 12.5 ml of THF, 25 ml of toluene, 10.0 g (64 mmol) of the alcohol prepared according to I. a) above and 0.5 g (70 mmol) of granulated lithium. The mixture was heated to 35° and a solution of 7.3 g (70 mmol) of styrene in 12.5 ml of THF was added dropwise by means of a "Perfusor IV" at 12 ml/h, keeping the temperature below or at 35° (the temperature decreased during the introduction). The whole was heated to reflux for 30 min until all the lithium disappeared and a solution of 8.8 ml (90 mmol) of methallyl chloride in 7.5 ml of DMSO was added dropwise at reflux. After heating at reflux for another 4 h, the reaction mixture was cooled down, poured on ice, extracted with ether, washed to neutrality with water, dried and concentrated. The raw product (32.3 g) was distilled on a 15 cm column filled with helices to give 9.6 g of 78% pure product consisting of a 79:21 mixture of, respectively, r-1,2,2,t-4-tetramethyl-c-3-(2-methyl-3-propenyloxy)-cyclohexane and r-1,2,2,c-4-tetramethyl-t-3-(2-methyl-3-propenyloxy)-cyclohexane. Further purification afforded the same mixture 97% pure.

Yield: 56%; B.p. 98°/17×10$^2$ Pa
IR: 3150, 2990, 1660, 1455, 1110, 900 cm$^{-1}$
NMR(360 MHz,$^1$H):
major isomer: 0.77(s,3H); 0.83(d,J=7 Hz,3H); 0.96(d,J=7 Hz,3H); 0.97(s,3H); 1.77(s,3H); 2.41(d,J=11 Hz,1H); 3.97(AB,J$_1$=11 Hz,J$_2$=40 Hz, 2H); 4.84(s,1H); 5.02(s,1H) δ ppm
minor isomer: 0.97(s,3H); 2.77(d,J=11 Hz,1H); 3.83(AB,J$_1$=11 Hz,J$_2$=25 Hz,2H); 4.84(s,1H); 5.00(s,1H) δ ppm
MS (major isomer): M$^+$=210(8)); m/e: 138(22), 96(25), 83(43), 69(48), 55(100), 43(52)
MS (minor isomer): M$^+$=210(8)); m/e: 138(24), 96(23), 83(39), 69(47), 55(100), 43(52)

b) In a mechanically stirred flask an ozone flow was bubbled for 1 h at −10° through a solution of 19.2 g (91 mmol) of the compound prepared in a) and 190 ml of methanol. In the meantime, a solution of 11.3 g (0.1 mol) of sodium sulfite in 90 ml of water was prepared in another flask and cooled to 0° (water/ice bath). The oxonide formed in the first flask was then introduced in the second one while maintaining the temperature at or below 20°. The reaction mixture was extracted with ether, washed with water, dried and concentrated to give 41.7 g of raw product. The latter was distilled on residue and identified by gas chromatography. A 83% pure product was thus obtained (16.4 g) consisting of a mixture containing 68% of 1-(2,2,c-3,t-6-tetramethyl-r-1-cyclohexyloxy)-2-propanone, 20% of 1-(2,2,t-3,t-6-tetramethyl-r-1-cyclohexyloxy)-2-propanone, 9% of 1-(2,2,t-3,c-6-tetramethyl-r-1-cyclohexyloxy)-2-propanone and 3% of 1-(2,2,c-3,c-6-tetramethyl-r-1-cyclohexyloxy)-2-propanone. A new purification of this mixture allowed its purity to be increased to 96%.

Yield: 70%; B.p. 56°/5.4 Pa
IR: 2940, 1720, 1450, 1350, 1100 cm$^{-1}$
isomer c-3,t-6 (68%)
NMR(360 MHz,$^1$H): 0.8(s,3H); 0.84(d,J=7 Hz,3H); 0.94(d,J=7 Hz,3H); 0.95(s,3H); 2.23(s,3H); 2.43(d,J=11 Hz,1H); 4.14(AB,J$_1$=18 Hz, J$_2$=25 Hz,2H) δ ppm MS: M$^+$=212(3); m/e: 155(10), 139(49), 83(100), 69(52), 55(49), 43(37)
isomer t-3,t-6 (20%)
NMR(360 MHz,$^1$H): 0.94(s,3H); 2.25(s,3H); 2.78(d,J=11 Hz,1H); 4.08(AB,J$_1$=15 Hz,J$_2$=8 Hz,2H) δ ppm
MS: M$^+$=212(3); m/e: 155(11), 139(50), 83(100), 69(65), 55(53), 43(40)
isomer t-3,c-6 (9%)
MS: M$^+$=212(2); m/e: 155(26), 139(30), 83(100), 69(56), 55(52), 43(38)
isomer c-3,c-6 (3%)
MS: M$^+$=212(2); m/e: 155(8), 139(40), 83(100), 69(52), 55(48), 43(39)

c) By oxidation of 1-(2,2,c-3,t-6-tetramethyl-1-cyclohexyloxy)-2-propanol

The desired propanone was also prepared by oxidation of the above-mentioned alcohol [see example 13)] as follows: a 3-neck flask equipped with a magnetic stirrer was charged with 9.1 g (42 mol) of PCC (pyridinium chlorochromate) and 10 ml of methylene chloride. A solution of 6.0 g (28 mmol) of the above-mentioned alcohol in 60 ml of methylene chloride was added dropwise while the temperature increased to 25°. The reaction mixture was left under stirring over the week-end at room temperature and then filtered on a SiO$_2$ column, washed with ether and concentrated. The raw product thus obtained (6.0 g) was distilled on a Vigreux column to give 3.6 g of a 86% pure propanone.

Yield: 52%; B.p. 51°/5.6×10$^2$ Pa

EXAMPLE 23

Preparation of a Perfuming Composition

A base perfuming composition of the floral type was prepared by admixture of the following ingredients:

| Ingredients | Parts by weight |
| --- | --- |
| Benzyl salicylate | 120 |
| EXALTEX ®[1] | 100 |
| IRALIA ®[2] | 100 |
| Phenylethyl alcohol | 100 |
| MAYOL ®[3] | 70 |
| HEDIONE ®[4] | 60 |
| p-tert-Butyl-cyclohexyl acetate | 50 |
| Benzyl acetate | 40 |
| Terpenyl acetate | 30 |
| Carbinol acetate | 30 |
| Distilled Madagascar clove essential oil | 25 |
| Heliotropin | 25 |
| Citronellol | 25 |
| Geranyl acetate | 20 |
| Cinnamic alcohol | 20 |
| 10%* Nonaldehyde | 20 |
| 10%* Anisic aldehyde | 15 |
| Coumarin | 15 |
| 1%* Ethylvanillin | 10 |
| 1%* Isobutylquinoline | 10 |
| Crystalline rosinol | 10 |
| 10%* β-Damascone | 5 |
| Total | 900 |

*in dipropyleneglycol (DIPG)
[1] pentadecanolide; origin: Firmenich SA, Geneva, Switzerland
[2] methylionone; origin: Firmenich SA, Geneva, Switzerland
[3] hydroxymethyl isopropyl cyclohexane; origin: Firmenich SA, Geneva, Switzerland
[4] methyl dihydrojasmonate; Firmenich SA, Geneva, Switzerland Eight perfume compositions were prepared with this base composition, two by admixture with two prior art perfuming ingredients, i.e. 1-(2,2,c-3,t-6-tetramethyl-r-1-cyclohexyl)-3-hexanol and 1-(2,2,3,6-tetramethyl-cyclohexyloxy)-2-pentanol [isomeric mixture containing around 51% of isomer (c-3,t-6), 28% of isomer (t-3,c-6) and 21% of isomer (c-3,c-6)], and the other six compositions by admixing the base composition with six preferred compounds of the invention. Table II below summarizes the constitution of said 8 compositions. In this table, the six compounds of the present invention are designated by their respective reference number appearing on Table I.

TABLE II

| Ingredients | Compositions | | | | | | | |
|---|---|---|---|---|---|---|---|---|
| | A | B | C | D | E | F | G | H |
| Floral base | 900 | 900 | 900 | 900 | 900 | 900 | 900 | 900 |
| 1%* 1-(2,2,c-3,t-6-tetramethyl-r-1-cyclohexyl)-3-hexanol | 10 | — | — | — | — | — | — | — |
| 10%* 1-(2,2,3,6-tetramethyl-cyclohexyloxy)-2-pentanol | — | 10 | — | — | — | — | — | — |
| 10%* 1) | — | — | 10 | — | — | — | — | — |
| 10%* 2) | — | — | — | 10 | — | — | — | — |
| 10%* 3) | — | — | — | — | 10 | — | — | — |
| 10%* 5) | — | — | — | — | — | 10 | — | — |
| 10%* 6) | — | — | — | — | — | — | 10 | — |
| 10%* 8) | — | — | — | — | — | — | — | 10 |
| Total | 910 | 910 | 910 | 910 | 910 | 910 | 910 | 910 |

*in DIPG

The addition of compounds 1), 2), 3), 5), 6) or 8) according to the invention to the base composition possessing a floral note afforded novel perfume compositions which developed richer and woodier notes, more interesting and rounder. This effect was noticed systematically with all the C to H compositions, when compared to the base composition.

The expert perfumers evaluated compositions C to H for comparison and showed a preference for the first three, i.e. compositions C, D and E, with a clear preference for composition C. The latter was also found to develop an odor note which was considered superior to that of composition B, more elegant and cleaner. A similar effect was noticed when comparing compositions D to H with composition B.

As regards composition A, the perfumers judged that compositions C to H could be used more easily, in spite of the fact that the perfuming ingredient in composition A was employed in a concentration ten times weaker than that of the other individual perfuming ingredients cited on Table II, so as to compensate for the remarkably strong odor of 1-(2,2,c-3,t-6-tetramethyl-r-1-cyclohexyl)-3-hexanol. Compositions C to E, in particular, were judged very interesting for an alternative use to that of composition A, since their odor turned out to be less aggressive, more refined and discrete than that of composition A, while keeping the warm and rich tonality of the woody-amber basic character.

EXAMPLE 24

Preparation of a Soap

To a soap base in chips, obtained from a sodium soap paste prepared from coconut and tallow oil, was added around 0.1 to 0.5% by weight, relative to the weight of soap paste and depending on the nature of the perfuming ingredient used, of one of the compounds according to the present invention. The original fat soap note was then found to be covered by an agreeable fragrance of the woody-amber floral type.

What I claim is:

1. A compound of formula

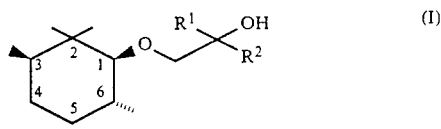

wherein $R^1$ represents a hydrogen atom or a saturated, linear or branched alkyl radical having from 1 to 4 carbon atoms; and $R^2$ designates a saturated or unsaturated, linear or branched lower alkyl radical.

2. A mixture comprising:

(a) a compound of formula

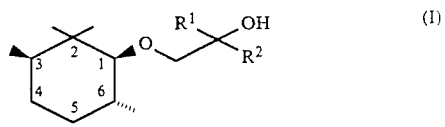

and b) an isomer of the compound of formula (I) above having the formula

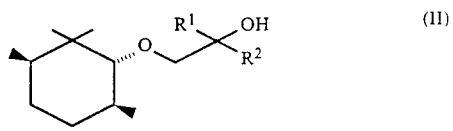

wherein, for each formula $R^1$ represents a hydrogen atom or a saturated, linear or branched alkyl radical having from 1 to 4 carbon atoms; and $R^2$ designates a saturated or unsaturated, linear or branched lower alkyl radical.

3. The mixture of claim 2 which comprises a predominant amount of the compound of formula (I).

4. The mixture of claim 2 which comprises at least about 75 wt. % of the compound of formula (I).

5. The mixture of claim 2 which further comprises at least one of a compound of formula

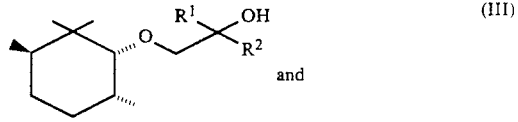

and

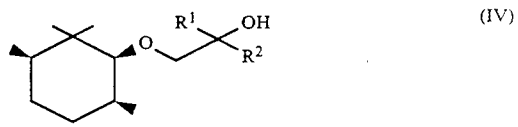

wherein $R^1$ and $R^2$ are as defined in claim 2 and wherein said at least one of compound III or IV is present in said mixture in an amount of no more than about 10 wt %.

6. A mixture comprising:

a) a compound of formula

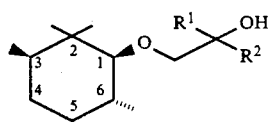 (I)

b) an isomer of formula (I) above having the formula

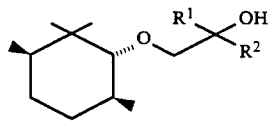 (II)

c) a compound of formula

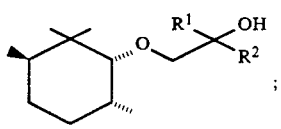 (III)

and
d) a compound of formula

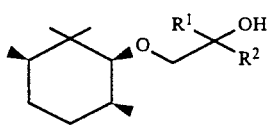 (IV)

wherein, for each formula
R$^1$ represents a hydrogen atom or a saturated, linear or branched alkyl radical having from 1 to 4 carbon atoms; and
R$^2$ designates a saturated or unsaturated, linear or branched lower alkyl radical.

7. The mixture of claim 6 which comprises a predominant amount of the composition of formula (I).

8. The mixture of claim 6 which comprises at least about 75 wt % of the compound of formula (I).

9. The mixture of claim 6 wherein compounds III and IV are each present in said mixture in an amount of less than about 10 wt %.

10. A compound selected from the group consisting of:
   a. 1-(2,2,c-3,t-6-tetramethyl-r-1-cyclohexyloxy)-2-pentanol;
   b. 1-(2,2,c-3,t-6,tetramethyl-r-1-cyclohexyloxy)-4-penten-2-ol;
   c. 1-(2,2,c-3,t-6,tetramethyl-r-1-cyclohexyloxy)-2-butanol; and
   d. a mixture comprising a predominant amount of any one of said compounds a–c with its corresponding isomer having the formula

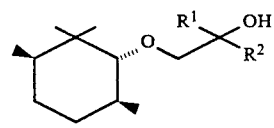 (II)

wherein
R$^1$ represents a hydrogen atom or a saturated, linear or branched alkyl radical having from 1 to 4 carbon atoms; and
R$^2$ designates a saturated or unsaturated, linear or branched lower alkyl radical.

11. The compound of claim 10, wherein said mixture comprises at least about 75 wt % of said predominant compound.

12. A method to confer, enhance, improve or modify the odor properties of a perfuming composition or a perfumed article, which method comprises adding to said composition or article a fragrance effective amount of a compound of formula I as defined in claim 1.

13. A method to confer, enhance, improve or modify the odor properties of a perfuming composition or a perfumed article, which method comprises adding to said composition or article a fragrance effective amount of the mixture of claim 3.

14. A method to confer, enhance, improve or modify the odor properties of a perfuming composition or a perfumed article, which method comprises adding to said composition or article a fragrance effective amount of the mixture of claim 7.

15. A perfuming composition comprising, as a perfuming ingredient, a compound of formula (I) as defined in claim 1.

16. A perfuming composition comprising, as a perfuming ingredient, the mixture of claim 3.

17. A perfuming composition comprising, as a perfuming ingredient, the mixture of claim 7.

18. A perfumed article comprising, as a perfuming ingredient, a compound of formula (I) as defined in claim 1.

19. A perfumed article comprising, as a perfuming ingredient, the mixture of claim 3.

20. A perfumed article comprising, as a perfuming ingredient, the mixture of claim 7.

21. A compound of formula

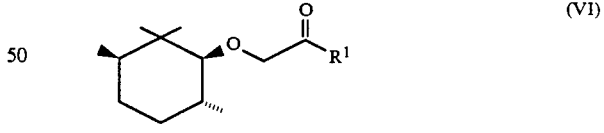 (VI)

wherein R$^1$ represents a hydrogen atom or a saturated linear or branched alkyl radical having from 1 to 4 carbon atoms.

* * * * *